(12) United States Patent
Suzuki et al.

(10) Patent No.: US 8,697,014 B2
(45) Date of Patent: Apr. 15, 2014

(54) SPECIMEN RACK

(75) Inventors: Kouichi Suzuki, Hitachinaka (JP);
Nobuo Suzuki, Hitachinaka (JP); Seiji Nomura, Tokai (JP); Tadashi Oishi, Ibaraki (JP); Takeshi Setomaru, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 200 days.

(21) Appl. No.: 13/058,049

(22) PCT Filed: Sep. 3, 2009

(86) PCT No.: PCT/JP2009/004342
§ 371 (c)(1),
(2), (4) Date: Feb. 17, 2011

(87) PCT Pub. No.: WO2010/035410
PCT Pub. Date: Apr. 1, 2010

(65) Prior Publication Data
US 2011/0182784 A1  Jul. 28, 2011

(30) Foreign Application Priority Data
Sep. 24, 2008 (JP) .................. 2008-243966

(51) Int. Cl.
*B01L 9/06* (2006.01)
(52) U.S. Cl.
USPC ......................................... 422/562; 206/443

(58) Field of Classification Search
USPC .......................................... 422/562; 206/443
See application file for complete search history.

(56) References Cited

U.S. PATENT DOCUMENTS 5,985,219 A * 11/1999 Lind ............................ 422/562
2003/0215370 A1    11/2003 Itoh

FOREIGN PATENT DOCUMENTS

| JP | 4-71169 U | 6/1992 |
| JP | 4-172250 A | 6/1992 |
| JP | 9-15246 A | 1/1997 |
| JP | 10-239321 A | 11/1998 |
| JP | 11-505920 A | 5/1999 |
| JP | 2003-326176 A | 11/2003 |
| JP | 2006-292696 A | 10/2006 |
| WO | 96/36437 A1 | 11/1996 |

* cited by examiner

*Primary Examiner* — Paul Hyun
(74) *Attorney, Agent, or Firm* — Mattingly & Malur, PC

(57) ABSTRACT

A specimen rack can be used for specimen containers irrespective of kinds thereof and irrespective of whether or not the specimen containers are rotated. An adapter is used for an automatic analyzer and a specimen pre-processing device and is adapted for a specimen rack capable of holding specimen containers. The adapter is provided with a specimen rack mounting section inserted and fixed to an adapter insertion section of a specimen rack body, a specimen container positioning section for holding the specimen containers, and a sleeve.

4 Claims, 5 Drawing Sheets

SPECIMEN RACK

This application is a national stage of PCT International Application No. PCT/JP2009/004342, filed Sep. 3, 2009, which claims priority to Japanese Patent Application No. 2008-243966, filed Sep. 24, 2008.

TECHNICAL FIELD

The present invention relates to a specimen rack using adapters.

BACKGROUND ART

A specimen rack for transporting multiple specimen containers is required for an automatic analyzer and a specimen pre-processing device because easy collection of liquid specimens improves efficiency.

Patent document 1 discloses a test tube support rack having a test tube support rack body having a cylindrical shape to support differently sized test tubes appropriately by use of one kind of test tube support rack and to transport each test tube separately depending on purposes of examinations and tests. A test tube insertion hole having a test tube support bottom is formed to a central portion of a circular cross section of the test tube support rack body in parallel to a central axis of the test tube support rack. A rack through hole smaller than a dimension of the test tube is provided to a central portion of the test tube support bottom.

Patent Document 2 discloses a specimen transport rack operable in both an automatic analyzer and a specimen pre-processing device and capable of accommodating various dimensions of specimen containers. The specimen transport rack includes a specimen rack capable of holding multiple specimen containers and an adapter having a generally ring shape and inserted into an insertion opening of a specimen container of the specimen rack. The adapter has a dimension generally the same as an inner diameter of the insertion opening of the specimen container provided to the specimen rack, and includes a specimen container positioning surface having an inner diameter generally the same as a dimension of a held specimen container and a specimen container pushing section projecting internally to the specimen container positioning surface.

Further, there is an automatic analyzer having a bar code reader for identifying specimens. In this case, since it is difficult to read the bar code during rotation of the specimen rack, it is necessary to control rotation of the specimen container.

On the other hand, since the bar code is read during the rotation in the specimen pre-processing device, it is necessary to rotate the specimen rack. Therefore, there are multiple specimen racks that accommodate sizes of the specimen containers and the presence or absence of the rotation of the specimen containers.

CITATION LIST

Patent Documents

Patent Document 1: Japanese Patent Laid-Open No. Hei 09-15246
Patent Document 2: Japanese Patent Laid-Open No. 2006-292696

SUMMARY OF THE INVENTION

Problem to be solved by the Invention

As mentioned above, there are the multiple specimen racks that accommodate types of the specimen containers and the presence or absence of the rotation of the specimen containers. Therefore, it is necessary for a user of the automatic analyzer and the specimen pre-processing device to provide the multiple specimen racks depending on the application. This results in problems of cost and a storage area.

An object of the present invention is to provide a common specimen rack regardless of types of the specimen containers and the presence or absence of the rotation of the specimen containers.

Means for Solving the Problem

A specimen rack adapter of the present invention is applied to a specimen rack capable of holding multiple specimen containers, the specimen rack being used for an automatic analyzer and a specimen pre-processing device. The adapter includes a specimen rack mounting section inserted and fixed to an adapter insertion section of a specimen rack body, a specimen container positioning section for holding the specimen containers, and a sleeve.

Advantages of the Invention

According to the present invention, cost can be reduced by providing a single type of specimen rack body and multiple specimen rack adapters.

Additionally, according to the present invention, the multiple specimen rack adapters are provided depending on the usage to mount different adapters to multiple holes. This permits handling of both the blood of elderly persons collected only by a trace amount and the blood of the other persons by use of the same specimen rack, improving operational efficiency.

Further, according to the present invention, easy attachment and detachment are achieved to improve convenience.

DESCRIPTION OF THE EMBODIMENTS

The present invention relates to a specimen rack using adapters and particularly to the specimen rack which is capable of transporting multiple specimen containers and which is particularly required to accommodate various sizes of specimen containers and the presence or absence of rotation of specimen containers in an automatic analyzer and a specimen pre-processing device which conduct urine analyses, biochemical analyses, and immunoassays by use of liquid specimens.

The present invention provides only one type of specimen rack body and multiple specimen rack adapters inserted into the specimen rack body. This achieves a specimen rack that accommodates sizes of specimen containers and the existence or absence of rotation of the specimen containers. Each specimen rack adapter is differently weighted to make constant the center of gravity of the specimen rack regardless of the specimen containers. Further, the specimen rack adapters used herein are mounted to and detached from a specimen rack body easily. Additionally, the use of a dedicated tool permits easier detachment.

Hereafter, embodiments of the present invention is explained in detail in reference to the drawings.

Embodiment

Figure 1:
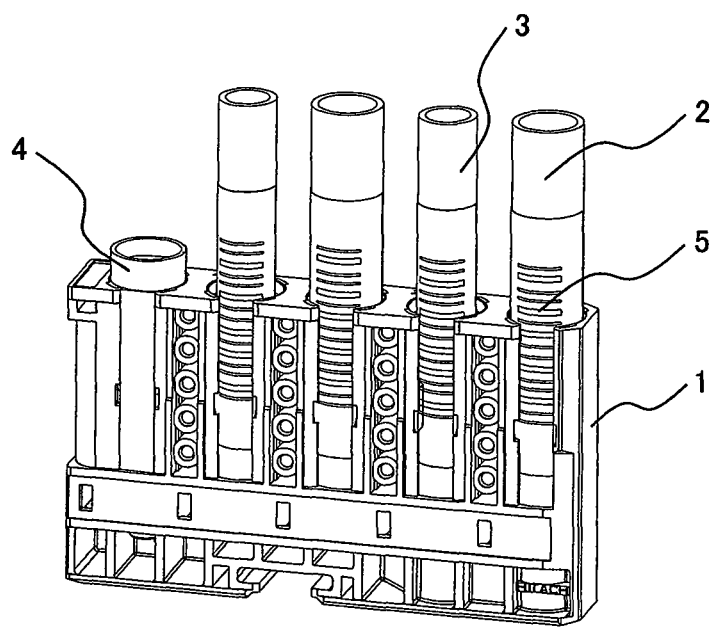
FIG. 1 is a perspective view showing a specimen rack of an embodiment of the present invention into which specimen containers have been inserted.

FIG. 1 is a perspective view showing the state where specimen containers have been inserted into a specimen rack of the present invention.

A 16 mm-diameter specimen container 2, a 13 mm-diameter specimen container 3 and a micro specimen container 4 have been inserted in a specimen rack body 1 of this embodiment. The specimen rack body 1 is a rectangular solid of 120 mm in length, 20 mm in width and 70 mm in height. Bar codes 5 for identifying specimens are affixed on the 16 mm-diameter specimen container 2 and the 13 mm-diameter specimen container 3.

The present invention is not limited to these sizes. In this figure, the number of the specimen containers mountable in the specimen rack body 1 is five, but the number is not limited to five. Additionally, the arrangement of the specimen containers is not limited to the above-mentioned embodiment.

Figure 2:
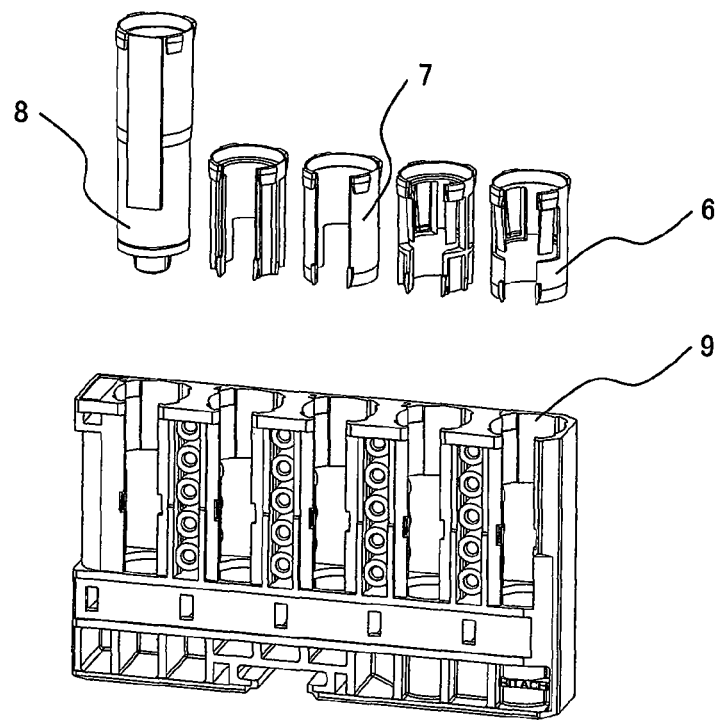
FIG. 2 is a perspective view showing the specimen rack and specimen rack adapters of the embodiment of the present invention.

FIG. 2 shows specimen rack adapters and the specimen rack body 1 used when the 16 mm-diameter specimen container 2, the 13 mm-diameter specimen container 3 and the micro specimen container 4 are inserted into the specimen rack body 1.

The specimen rack adapters are generally ring-shaped, each of which has a side surface not completely closed but partially opened. This permits, e.g., the bar codes affixed to the side surfaces of the specimen containers to be read. Herein, the shape of the partially opened side surface of the specimen rack adapter is called a C-shape.

The specimen rack adapters vary depending on sizes of the specimen containers and the existence or absence of rotation of the specimen containers, and include a rotation restricting adapter 6, a rotation adapter 7 and an adapter for both micro specimen container and 13 mm-diameter specimen container 8, and can be inserted into five holes of the specimen rack body 1 freely. The rotation restricting adapter 6, the rotation adapter 7, and the adapter for both micro specimen container and 13 mm-diameter specimen container 8 are inserted from adapter insertion sections 9 of the specimen rack body 1.

The inner diameters of the specimen rack adapters are a little smaller than but generally equal to the outer diameters of the specimen containers. This prevents the specimen containers mounted in the specimen rack adapters from being damaged by vibration etc.

Figure 3:
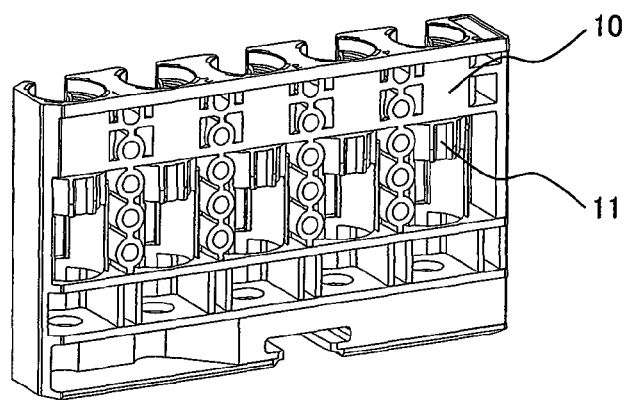
FIG. 3 is a perspective view showing the specimen rack of the embodiment of the present invention into which the specimen rack adapters has been inserted.
Figure 4A:
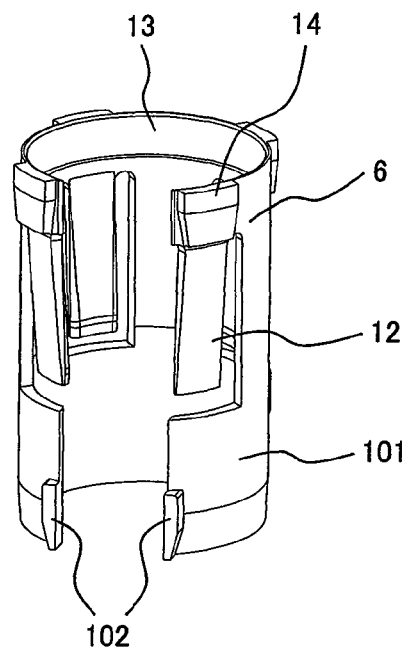
FIG. 4A is a perspective view showing a specimen container rotation restricting adapter of an embodiment of the present invention.
Figure 4B:
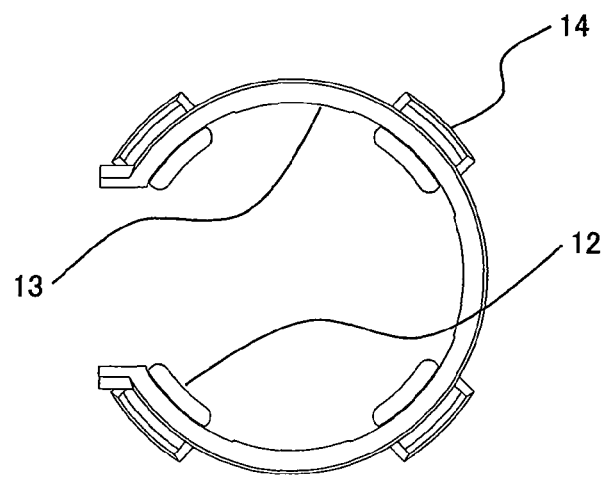
FIG. 4B is a top view showing the specimen container rotation restricting adapter of the embodiment of the present invention.
Figure 5A:
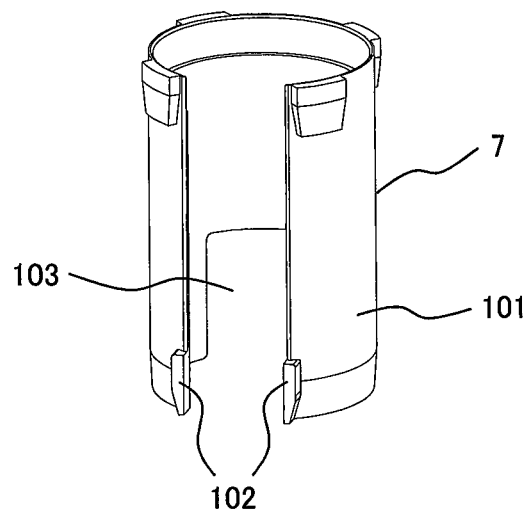
FIG. 5A is a perspective view showing a specimen container rotation adapter of an embodiment of the present invention.
Figure 5B:
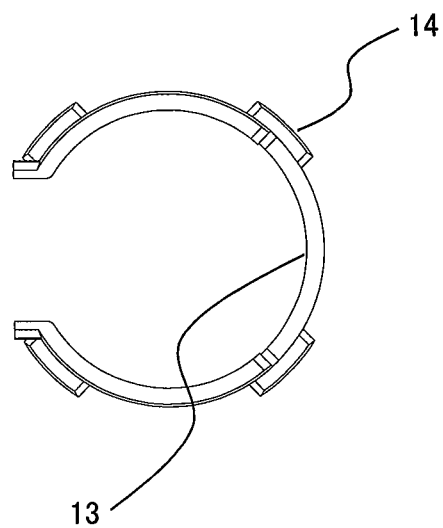
FIG. 5B is a top view showing the specimen container rotation adapter of the embodiment of the present invention.
Figure 6A:
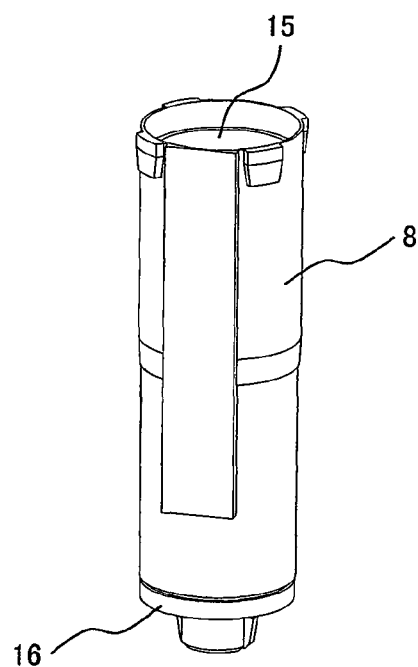
FIG. 6A is an upper perspective view showing a combined micro specimen container and 13 mm-diameter specimen container adapter of an embodiment of the present invention.
Figure 6B:
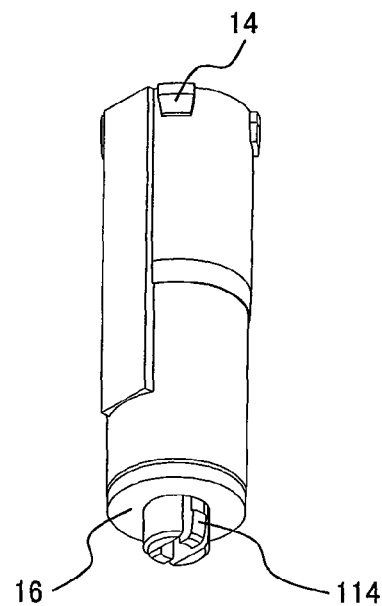
FIG. 6B is a lower perspective view showing the combined micro specimen container and 13 mm-diameter specimen container adapter of the embodiment of the present invention.

FIG. 3 is a perspective view showing the specimen rack of the embodiment of the present invention into which the specimen rack adapters have been inserted. FIG. 4A is a perspective view showing the specimen container rotation restricting adapter of an embodiment of the present invention, and FIG. 4B is its top view. FIG. 5A is a perspective view showing the specimen container rotation adapter of an embodiment of the present invention, and FIG. 5B is its top view. FIG. 6A is a top perspective view showing an adapter for both micro specimen container and 13 mm-diameter specimen container of an embodiment of the present invention. FIG. 6B is its lower perspective view.

As shown in FIGS. 4A and 4B, a rotation restricting adapter 6 has specimen container pushing sections 12 on a middle portion thereof, the specimen container pushing sections 12 restricting the rotation of the specimen container. In this embodiment, the specimen container is pushed at four places. Accordingly, the specimen container can be fixed and its rotation can be restricted. The specimen container is held by the specimen container pushing sections 12 and a specimen container positioning section 13. The specimen container is preferably but not limited to be held vertically to the upper surface of the adapter insertion section 9 shown in FIG. 2. The rotation restricting adapter 6 is mounted (secured) to the specimen rack body 1 by inserting specimen rack mounting sections 14 into the adapter insertion section 9 shown in FIG. 2.

In this embodiment, the specimen rack mounting sections are provided to four upper portions of the rotation restricting adapter 6. Accordingly, the rotation restricting adapter 6 is certainly fixed to the specimen rack body 1. The specimen rack mounting sections 14 are tapered such that their lower ends are not snagged on the specimen rack body 1 when inserted into the specimen rack body 1.

In this embodiment, a sleeve 101 is provided to the rotation restricting adapter 6 such that a user can insert the rotation restricting adapter 6 into the specimen rack body 1 safely and easily. The outer circumference of the lower end of the sleeve 101 is tapered. This produces a space between the rotation restricting adapter 6 and the specimen rack body 1 to insert the rotation restricting adapter 6 into the specimen rack body 1 easily.

Further, two knobs 102 are provided to the sleeve 101, and the lower ends of the knobs 102 are tapered. The rotation restricting adapter 6 can be detached from the specimen rack body 1 safely and easily by inserting a tweezers-like jig into spaces produced between these tapers and specimen rack body 1 and pinching the two knobs 102.

As shown in FIGS. 5A and 5B, the rotation adapter 7 holds the specimen container by use of the specimen container positioning section 13. The rotation adapter 7 is mounted in the same manner as the rotation restricting adapter 6 shown in FIGS. 4A and 4B. The sleeve 101 and the knobs 102 are also the same as those of the embodiment shown in FIGS. 4A and 4B.

In this embodiment, to permit the specimen container to rotate, the rotation adapter 7 does not have the specimen container pushing section 12 shown in FIGS. 4A and 4B. This reduces friction between the specimen container and the specimen container positioning section 13 to permit the easy rotation.

To accommodate a rotation mechanism of the specimen pre-processing device, a notch section 103 is provided to the rotation adapter 7.

The adapter for both micro specimen container and 13 mm-diameter specimen container 8 shown in FIGS. 6A and 6B is used in transporting the micro specimen container 4 and the 13 mm-diameter specimen container 3. Since the micro specimen container 4 of FIG. 1 is lighter than the 16 mm-diameter specimen container 2 and the 13 mm-diameter specimen container 3, the specimen rack may fall during transport due to uneven weight distribution.

Then, as shown in FIGS. 6A and 6B, a weight 16 is detachably mounted (attached) to the bottom of the adapter for both micro specimen container and 13 mm-diameter specimen container 8. This provides even weight distribution on the specimen rack. Herein, the whole of the specimen rack can be compact when the weight 16 is made of metal because its volume can be small, but its material is not limited to metal but may be resin.

Further, to prevent the bottom of the adapter for both micro specimen container and 13 mm-diameter specimen container 8 from being unstable due to the attachment of the weight 16 made of metal, a weight securing section 114 is provided to the bottom of the adapter for both micro specimen container and 13 mm-diameter specimen container 8.

The adapter for both micro specimen container and 13 mm-diameter specimen container 8 has a micro specimen container insertion hole 15 into which a micro specimen container is inserted. Since the adapter for both micro specimen container and 13 mm-diameter specimen container 8 has a cylindrical shape whose side surface is closed, this shape is called an O-shape.

When the 16 mm-diameter specimen container 2 and the 13 mm-diameter specimen container 3 are inserted into the same specimen rack body 1 and introduced to a centrifuge, the centrifuge may stop. To address this problem, when the 16 mm-diameter specimen container 2 and the 13 mm-diameter specimen container 3 are introduced to the centrifuge, the adapter for both micro specimen container and 13 mm-diameter specimen container 8 is mounted to a mounting position for the 13 mm-diameter specimen container 3 in the specimen rack body 1.

In the past, although the specimen rack body 1 used in an automatic analyzer is different from that used in a specimen pre-processing device, the specimen rack can be used in both the automatic analyzer and the specimen pre-processing device by setting a height of the specimen rack side surface 10 to 70 mm from its upper surface as shown in FIG. 3. Further, the specimen rack adapters 11 are provided lower than the height of the specimen rack side surface 10, so that specimens managed using barcodes can be selected using colors of the specimen rack adapters by providing color sensors to the automatic analyzer and the specimen pre-processing device.

INDUSTRIAL APPLICABILITY

The specimen rack adapters of the present invention are applicable to automatic analyzers, specimen pre-processing devices etc.

DESCRIPTION OF REFERENCE NUMERALS

1: Specimen rack body
2: 16 mm-diameter specimen container
3: 13 mm-diameter specimen container
4: Micro specimen container
5: Bar code
6: Rotation restricting adapter
7: Rotation adapter
8: Adapter for both micro specimen container and 13 mm-diameter specimen container
9: Adapter insertion section
10: Specimen rack side surface
11: Specimen rack adapter
12: Specimen container pushing section
13: Specimen container positioning section
14: Specimen rack mounting section
15: Micro specimen container Insertion hole
16: Weight
101: Sleeve
102: Knob
103: Notch section
114: Weight securing section

The invention claimed is:

1. A specimen rack adapter applied to a specimen rack which is used for an automatic analyzer and a specimen pre-processing device and which is capable of holding a plurality of specimen containers, the specimen rack having a plurality of holes for inserting the specimen containers therein,
the specimen rack adapter comprising:
a specimen rack mounting section insertable to become fixed to an adapter insertion section of the specimen rack;
a specimen container positioning section for holding one of the specimen containers; and
a sleeve for easy insertion of the specimen container positioning section into the specimen rack,
wherein the sleeve has a partially opened side surface, and has two knobs at a lower end thereof, the knobs being exposed from the specimen rack in a state of being inserted into one of the holes,
wherein the sleeve has a notch section for accommodating a rotation mechanism of the specimen pre-processing device, and
wherein the knobs are tapered at lower ends thereof.

2. The specimen rack adapter according to claim 1, further comprising:
a plurality of protrusions for fixing the specimen container on an inner periphery of the specimen rack adapter.

3. The specimen rack adapter according to claim 1,
wherein pinching the knobs detaches the specimen rack adapter from the specimen rack body when in the state of being inserted in one of the holes.

4. The specimen rack adapter according to claim 1,
wherein an outer circumference of the lower end of the sleeve is tapered for producing a space between the specimen rack adapter and the specimen rack.

* * * * *